(12) United States Patent
Polavarapu et al.

(10) Patent No.: US 9,365,880 B2
(45) Date of Patent: Jun. 14, 2016

(54) FERMENTATION PROCESS FOR THE PRODUCTION OF RAPAMYCIN

(75) Inventors: Baby Rani Polavarapu, Banjara Hills (IN); Suneel Kumar Battula, Banjara Hills (IN); Kali Satya Bhujanga Rao Adibhatla, Banjara Hills (IN); Venkaiah Chowdary Nannapaneni, Banjara Hills (IN)

(73) Assignee: Natco Pharma Limited, Banjara Hills, Hyderabad (IN)

( * ) Notice: Subject to any disclaimer, the term of this patent is extended or adjusted under 35 U.S.C. 154(b) by 0 days.

(21) Appl. No.: 14/391,000

(22) PCT Filed: Apr. 12, 2012

(86) PCT No.: PCT/IN2012/000262
§ 371 (c)(1),
(2), (4) Date: Oct. 6, 2014

(87) PCT Pub. No.: WO2013/153554
PCT Pub. Date: Oct. 17, 2013

(65) Prior Publication Data
US 2015/0079642 A1    Mar. 19, 2015

(51) Int. Cl.
*C12N 1/20* (2006.01)
*C12P 17/18* (2006.01)
*C12R 1/55* (2006.01)

(52) U.S. Cl.
CPC ............ *C12P 17/189* (2013.01); *C12P 17/188* (2013.01); *C12R 1/55* (2013.01)

(58) Field of Classification Search
None
See application file for complete search history.

(56) References Cited

U.S. PATENT DOCUMENTS

| 3,929,992 A | 12/1975 | Sehgal et al. |
| 3,993,749 A | 11/1976 | Sehgal et al. |
| 5,100,899 A | 3/1992 | Calne |

FOREIGN PATENT DOCUMENTS

| WO | 93/22446 A1 | 11/1993 |
| WO | 2004/022767 A1 | 3/2004 |

OTHER PUBLICATIONS

Fang et al., "Exogenous Shikimic Acid Stimulates Rapamycin Biosynthesis in *Streptomyces hygroscopicus*," Folia Microbiol., 1995, vol. 40(6), pp. 607-610.
Martel et al., "Inhibition of the immune response by rapamycin, a new antifungal antibiotic," Can. J. Physiol. Pharmacol., 1977, vol. 55, pp. 48-51.
Vezina et al., "Rapamycin (AY-22,989), A New Antifungal Antibiotic," J. Antibiotics, 1975, vol. 28, pp. 721-725.
Zhu et al., "Generation of High Rapamycin Producing Strain via Rational Metabolic Pathway-Based Mutagenesis and Further Titer Improvement with Fed-Batch Bioprocess Optimization," Biotechnology and Bioengineering,Oct. 2010, vol. 107(3), pp. 506-515.
International Search Report, Nov. 23, 2012, PCT application No. PCT/IN2012/000262, 2 pages.

*Primary Examiner* — Iqbal H Chowdhury
(74) *Attorney, Agent, or Firm* — Mintz, Levin, Cohn, Ferris, Glovsky and Popeo, P.C.

(57) ABSTRACT

The present invention provides a novel method for producing rapamycin by submerged fermentation which comprises cultivating *Streptomyces hygroscopicus* (CBS 773.72) and mutants thereof. The present invention provides a high yielding mutant culture MTCC5681 from *Streptomyces hygroscopicus* CBS 773.72. This culture is capable of producing rapamycin more efficiently than the cultures *Streptomyces hygroscopicus* from sources like ATCC, NRRL etc which have been reported so far.

13 Claims, No Drawings

FERMENTATION PROCESS FOR THE PRODUCTION OF RAPAMYCIN

FIELD OF THE INVENTION

This invention relates to a mutant culture of *Streptomyces hygroscopicus* capable of producing rapamycin. A viable sample of mutant strain is currently deposited at the Microbial Type Culture Collection and Gene Bank (MTCC) under accession number MTCC 5681. The novel mutant strain provided herein is hereinafter referred to as *Streptomyces hygroscopicus* MTCC 5681. Rapamycin of the present invention is produced by fermentation of a *Streptomyces hygroscopicus* MTCC 5681 in a nutrient medium.

BACKGROUND OF THE INVENTION

Rapamycin (U.S. Pat. Nos. 3,929,992 and 3,993,749) was reported as an antifungal antibiotic which was produced by *Streptomyces hygroscopicus* AY B-994 (ATCC 29253) (C. Vezina, A. Kudelski and S. N. Sehgal J. Antibiotics 28, 721-726, 1975). In recent years, it has been demonstrated that rapamycin shows potent immunosuppressive activity (Martel R. R. et al can. J. physiol. pharmcol. 55, 48-51, 1977). Rapamycin has been shown to be effective in inhibiting transplant rejection (U.S. patent application ser. no. 362, 544 filed Jun. 6, 1989). Rapamycin is widely used as an immunosuppressant in organ transplant recipients and has shown limited toxicities even in combination with other immunosupressants like cyclosporine or corticosteroids. The intracellular rapamycin receptor is a small protein termed FKBP12 (FK506-binding protein). The FKBP-rapamycin complex inhibits the function of a serine/threonine kinase, mTOR (mammalian target of rapamycin). In addition, rapamycin has in vitro and in vivo activity against a broad range of human tumor cell lines and considered to represent a promising new class of cytostatic anticancer agents.

The microbial process of rapamycin by aerobic fermentation of submersion culture of the new species Actinoplanes is described in WO9322446. Fermentation conditions like dissolved oxygen and air flow are not discussed. The titer of rapamycin produced by this organism is 405 mg/L only.

A method for producing rapamycin by solid state fermentation is disclosed in WO 2004/022767. The solid state fermentation process is difficult to adopt for larger volumes and scale up to commercial quantities. Determination of yield, titer value and biomass are difficult in this method. Substrates require pretreatment and it is very difficult to monitor process parameters like pH, dissolved oxygen and biomass concentrations, thus introducing batch to batch variations.

The present invention provides a titer value of 900 mg/L for rapamycin. A method for producing rapamycin by culturing the organism in an aqueous nutrient and novel fermentation media containing shikimic acid and allows the organism to produce the product in high yields. The process is well characterized with specifically identified process and engineering parameters to facilitate manufacture of rapamycin on a commercial scale.

BRIEF DISCLOSURE OF THE INVENTION

The present invention is directed to a mutant strain *Streptomyces hygroscopicus* MTCC 5681 capable of producing rapamycin by a novel process.

The present invention also is directed to a mutant strain *Streptomyces hygroscopicus* MTCC 5681 capable of producing rapamycin more efficiently than *streptomyces hygroscopicus* from other sources which have been reported in the prior art.

Furthermore, the present invention is aimed at a fermentation process in aqueous nutrient medium comprising assimilable sources of carbon and nitrogen. The fermentation is carried out by incorporation of shikimic acid as precursor in media composition to increase the productivity of rapamycin. The fermentation is also carried out in a fed batch mode for enhancing productivity and yield of rapamycin.

DETAILED DESCRIPTION OF THE INVENTION

The rapamycin-producing organism used for this invention *streptomyces hygroscopicus* CBS 773.72 was purchased from Centraalbureau voor Schimmelcultures, fungal biodiversity centre, Institute of the Royal Netherlands Academy of Arts and sciences, the Netherlands. It is to be understood that the invention is not limited to the use of the particular organism here in described, but includes variations and mutants obtained by natural selection or by treatment of the microorganism with, for instance, ultraviolet rays, X-rays, N-methyl-N'-nitro-N-nitroso-guanidine.

In order to isolate the mutant strain suitable for the purpose of this invention, the aforesaid strain which is known to produce rapamycin is subjected to mutation treatment. *Streptomyces hygroscopicus* CBS773.72 strain is inoculated to a slope of ME agar (1% malt extract, 0.4% yeast extract, dextrose 0.4% agar 2%, pH 7.0) and cultured at 28° C. for a week. The deposited spores are collected by scraping, taken into 5 ml of a sterile 0.1 M Tris-HCl buffer (pH 8.5 containing 1 mM EDTA), subjected to ultrasonic treatment (15 seconds on a ultrasonic vibra cell, model VCX500) and passed through a small glass tube packed with sterilized absorbent cotton to obtain 4.5 ml of an almost pure uniform spore solution. 0.5 ml of an aqueous solution of N-methyl-N'-nitro-N-nitroso-guanidine (NTG) of a concentration of 10 mg/ml is added to effect the mutation treatment at 28° C. for 60 minutes while shaking slowly. The killing rate at that time was 92.6%. After the treatment, it is diluted appropriately with sterilized physiological saline, then 0.1 ml of an aliquot is plated on a petridish plate obtained by solidifying the ME agar and cultured at 28° C. for 7 days. The produced colonies are isolated into ME agar slope and cultured, and the rapamycin generated is tested by the procedures described below. The concentration of rapamycin is measured and monitored.

Firstly, one ml of the above isolated strain is inoculated to a 500 ml Erlenmeyer flask to which 50 ml of sterile seed culture medium set forth below has been added and shake cultured on a rotary shaker at 28° C. for 4 days.

| Medium for seed culture (w/w concentrations in aqueous medium) | |
|---|---|
| Dextrose | 2% |
| Ammonium sulphate | 0.3% |
| Calcium carbonate | 0.15% |
| Soya bean meal | 4% |
| Distilled water | pH 6.8 |

Thereafter, 5 ml is inoculated to a 250 ml Erlenmeyer flask to which 20 ml of the main culture medium set forth below has been added and sterilized and shake cultured on a rotary shaker at 28° C. for 12 days.

| Medium for main culture (w/w concentrations in aqueous medium) | |
| --- | --- |
| Dextrose | 2% |
| Ammonium sulphate | 0.1% |
| Potassium dihydrogen phosphate | 0.5% |
| Soya bean meal | 3% |
| Distilled water | pH 6.8 |

One ml of the broth is sampled from each culture flask, 5 ml of methanol is added thereto and stirred on a thermomixer, after which the product is extracted into the liquor layer. The supernatant and the microbial cells are separated by filtration; supernatant fraction is carried out in BDS Hypersil C18 column, 150 mm×4.6 mm, 5 µm, at 60° C. The detection wavelength of UV lamp is set at 260 nm in isocratic profile. The mobile phase is acetonitrile in ammonium acetate buffer solution with 1ml/min flow rate and compared with rapamycin standard product (rapamycin standard prepared by the Fujian institute of microbiology). Product concentration in terms of potency/titer value is assessed by comparing the areas of peaks of fermentation extraction fractions of the parent strain and the mutant strain by a suitable HPLC method.

The mycological properties of mutant strain *Streptomyces hygroscopicus* MTCC 5681 which is one of the strains thus obtained are shown below.

1. Morphology

Mutant stain *Streptomyces hygroscopicus* MTCC 5681 forms monopodially branched aerial mycelium; sporophores are terminated by spore chains in the form of short, narrow, compact and closed coils of three or more turns. Ten or more spores are present in each spiral and spore color is predominantly gray and turning gray-brown on prolonged incubation. Aerial mycelium is hygroscopic: on absorption of water, spores crowd in masses and a black pigment is produced. Black, gelatinous spots appear on the surface of several solid media and the spores are oval and smooth.

Growing Conditions in Various Media

Tomato Paste Oatmeal Agar: Rapid and abundant vegetative mycelium. More aerial mycelium with gray spores and black spots. No pigmentation.

Tryptone Yeast Extract Agar (ISP Medium1): Rapid and abundant growth. Moderate aerial mycelium, spores yellowish with black spots and yellow pigmentation.

Yeast Extract—Malt Extract Agar (ISP Medium 2): Rapid and abundant growth. Moderate aerial mycelium and spores white to gray with black spots. Yellow pigmentation.

Oatmeal Agar (ISP Medium 3): Very abundant growth. More Aerial mycelium, spores white to gray with black spots and pale yellow pigmentation.

Inorganic Salts—Starch Agar (ISP Medium 4): Slow growth. Moderate aerial mycelium, spores white to gray with some black spots. No soluble pigmentation.

Glycerol-Asparagine Agar (ISP—Medium 5): Slow growth. Very poor aerial mycelium, spores gray to beige with no black spots. Pigmentation Pale pink.

Peptone-Yeast Extract-Iron Agar (ISP Medium 6): Poor growth. No sporulation. Yellow pigmentation.

Czapek's Solution Agar (Waksman's Medium 1): Slow growth poor sporulation. No pigmentation.

Glucose—Asparagine Agar (Waksman's Medium 2): Rapid and abundant growth. Moderate aerial mycelium and spores white to yellowish with black spots. Pale yellow pigmentation.

Bennett's Agar: Very abundant growth. Moderate aerial mycelium and spores white to yellowish with black spots. Yellow pigmentation.

Potato Sucrose Agar: Moderate growth. Spores white to gray with black spots. Yellow pigmentation Sabouraud Dextrose Agar: Rapid and abundant growth. No sporulation and no pigmentation.

Sabouraud Maltose Agar: Rapid and abundant growth. No sporulation and no pigmentation.

Physiological Properties

Growth Temperature Relation

The results of tests at 20° C., 25° C., 28° C., 33° C., 37° C. and 46° C. revealed that the growth was possible at temperature in the range (20° C.-46° C.), but optimum temperature was observed to be in the vicinity of 25° C. to 33° C. The observed growth trend is as follows.

| 20° C. | 25° C. | 28° C. | 33° C. | 37° C. | 46° C. |
| --- | --- | --- | --- | --- | --- |
| Less growth | Excellent growth | Excellent growth | Good growth | Less growth | No growth |

Hydrolysis of starch (ISP medium 4 culture at 28° C.) hydrolyzes starch slow, but eventually extensive Liquefication of gelatin (glucose—peptone-gelatin medium, culture at 20° C.) liquefies.

Coagulation and peptonization of defatted milk (defatted milk medium, culture at 28° C.) coagulation and clearing of milk.

Generation of Hydrogen sulphide ($H_2S$): Hydrogen sulphide is not generated.

Formation of Melanin like dyes (tyrosine agar ISP 7 medium culture at 28° C.) melanin like dyes are hardly formed or even when formed only a trace is observed.

Nitrate reduction (ISP medium 8): Very weakly positive or nitrate not reduced to nitrite.

Decomposition of cellulose: No disintegration on both Jensen's cellulose broth, Levine and schoenlein's cellulose broth.

Carbohydrate utilization: Good growth on glucose, fructose, mannitol, inositol, soluble starch and glycerol. Moderate growth on xylose, arabinose, rhamnose, raffinose, lactose and maltose. No growth on sucrose and cellulose.

pH relations: Growth at pH 5 to 7.5. Optimal growth at pH 5.5 to 7.0. No growth at pH 4 and above 8.

Spores or hyphae of the aforesaid mutant stain *Streptomyces hygroscopicus* MTCC 5681 on inoculation in a medium containing nutrient sources proliferate aerobically. The nutrient sources consist of utilizable sources of assimilable carbon for the production of rapamycin and are very diverse, including sugars (glucose, fructose mannitol and the like) dextrins, starches of different types, glycerol, inositol and vegetable fats. The sources of organic assimilable nitrogen which actively stimulate growth and favor production of rapamycin are substances such as soya bean meal, cotton seed meal; corn steep liquor, yeast extract, peptone and inorganic nitrogens such as ammonium sulphate, ammonium chloride, ammonium nitrate and ammonium phosphate. Additionally according to necessity inorganic salts such as table salt, potassium chloride, carbonates, other heavy metal salts, phosphates of sodium, potassium, ammonium and calcium and vitamins are included in appropriate concentrations. The nutritive medium contains a number of trace elements such as magnesium, iron, manganese and zinc. It is also possible to appropriately add defoamer such as poly propylene glycols of suitable grade. The addition of shikimic acid with appropriate concentration can increase the amount of rapamycin significantly.

Fermentation of mutant strain *Streptomyces hygroscopicus* MTCC 5681 is carried out as follows. In small scale fermentations, mutant strain *Streptomyces hygroscopicus* MTCC 5681 is inoculated in sterilized medium. The fermentation conditions such as the temperature, pH, airflow, stirring and fermentation time are selected under submerged conditions. It is advantageous to conduct the fermentation at temperatures in the range 20° C. to 37° C., preferably 28° C., at a pH 5-7.5, preferably 6.0, for 10-15 days, preferably 12 days. Larger scale fermentations may be carried out as follows. Mutant strain *Streptomyces hygroscopicus* MTCC 5681 is inoculated in sterilized medium, grown at a temperature 20° C. to 37° C., preferably 28° C. for 4 days and later at 25° C. till the end of fermentation process for 10-15 days, preferably 12 days under submerged conditions with agitation 100 to 500 rpm preferably 150 to 350 rpm. The preferred aeration condition is 0.3 to 1.5 VVM. The pH is controlled during fermentation in reactors and maintained at about 6.0 and glycerol starch solution or precursor shikimic acid is added continuously from about 4 days after beginning to the end of fermentation, thus obtaining maximum yields in about 12 days.

It has been observed that the productivity of the mutant strain *Streptomyces hygroscopicus* MTCC 5681 is surprisingly better than that of *Streptomyces hygroscopicus* CBS 773.72. The variants and mutants of *Streptomyces* sp. are obtained by natural selection and by artificial treatments which produce rapamycin.

The advantages of the present invention over the other reported methods are
 (i) Higher titer value of rapamycin using mutant strain *Streptomyces hygroscopicus* MTCC 5681 obtained from *Streptomyces hygroscopicus* CBS 773.72
 (ii) Incorporation of shikimic acid as a precursor in production media composition thereby facilitating and accelerating the generation of maximum amount of rapamycin in fermentation broth.
 (iii) Fed batch submerged fermentation process with 60% glycerol or 10% starch solution or 10% shikimic acid solution feeding to maintain pH 6.0. By continuously maintaining the fermentation batch mix at pH 6.0 the productivity and yield of rapamycin is much higher.

Materials and Methods
Microorganism

*Streptomyces hygroscopicus* strain used in this study was CBS 773.23, obtained from the centraalbureau voor schimmelcultures (CBS) Netherlands. The strain was maintained on yeast extract-malt extract agar—ME agar slants at 4° C. and sub cultured monthly Media All media were sterilized by autoclaving at 121° C. and the pH was adjusted before sterilization. The following culture media were employed throughout the work. Yeast extract—malt extract agar—ME agar was employed for slant and plate cultures.

ME agar contained (g/l): yeast extract 4.0; malt extract 10; dextrose 4.0

Preparation of Spore Suspension:

The spores were brushed aseptically into 5 ml saline water from the ME slants grown for 11-13 days at 28° C. The 5 ml spore solution was mixed thoroughly on vortex mixer. Spore suspension was diluted to $1 \times 10^6$ spores/ml in saline and stored at 6-8° C.

UV Irradiation

Five milliliter spore suspension contained in a Petri dish was placed under an ultraviolet lamp (15 W, 2537 Å) at a distance of 15 to 30 cm, and was irradiated for different time intervals between 15 sec to 30 min. Treated and untreated spores were diluted in sterile physiological saline, and 1 ml spore suspension was spread on to single colony isolation medium to calculate the percentage survival. Samples with a death rate of more than 90% were subjected to subsequent isolation. The death ratios of treated strains were increased with treating time and mutation induced with high death rate.

NTG (Nitrosoguanidine) Treatment 1 ml of NTG solution (10 mg/ml, 0.2 M pH 6.0 phosphate buffer) was added in 1 ml spore suspension. After incubation at 28° C. on a rotary shaker of 120 rpm for different time intervals between 30 and 180 min, the mixture was diluted 1000 times with sterile water immediately. Treated and untreated spores were diluted in sterile physiological saline, and 1 ml spore suspension was spread on to the single colony isolation medium (ME) to calculate the percentage survival. Samples with a death rate of more than 90% were subjected to subsequent isolation. The plates were incubated at 28° C. temperature for 11-12 days and the mutants were selected on the basis of morphological characteristics on plate media.

Analytical Methods

Cell concentration was determined by packed mycelial volume measurement using 10 ml of the fermented broth from the culture flask and centrifuging at 3000 RPM for 10 minutes. The detection of Rapamycin was carried out by HPLC method. The fermented broth was extracted with methanol (Methanol and Broth in ratio of 1:5) and HPLC analysis was carried out in BDS Hypersil C18 column, 150 mm×4.6 mm, 5 µm, column temperature 60° C., detection wavelength of UV lamp 260 nm in isocratic profile having the mobile phase acetonitrile and 0.7708 g/l of ammonium acetate buffer solution with 1 ml/min flow rate.

EXPERIMENTAL DESIGN

Media composition experiments were designed to meet the nutritional demands of the strain NRC-SH-03. The carbon source, nitrogen source, precursors and pH were regarded as correlated factors of the culture medium.

The following examples are given for the purpose of illustrating the present invention and should not be construed as being limitations on its scope.

Example 1

Mutagenesis of Strain of *Streptomyces hygroscopicus* CBS 773.72

Preparation of spore suspension: Sporulated mycelium was grown on a ME agar comprising 1% malt extract, 0.4% yeast extract, dextrose 0.4% agar 2%, pH 7.0. The spores were collected by scraping, taken into 5 ml of an aseptic 0.1 M Tris-HCl buffer (pH 8.5 containing 1 mM EDTA), then subjected to the ultrasonic treatment (15 seconds on a ultrasonic vibra cell, model VCX500) and passed through a small glass tube packed with sterilized absorbent cotton to obtain 4.5 ml of an almost uniform spore suspension.

Influencing by NTG 1 ml of spore suspension showing the spore number of $10^6$/ml and 0.5 ml of an aqueous solution of N-methyl-N'-nitro-N-nitroso-guanidine (NTG) of a concentration of 10 mg/ml and containing minimal amount of dimethyl formamide were added to 8.5 ml of saline solution. NTG concentration in the specified solution was 0.5 mg/ml and spore density of the order of $10^5$ spores/ml.

The biological material, while continuously stirred was influenced at 28° C. for 60 minutes. A 1 ml was sampled every 10 minutes. The sample was centrifuged quickly and the influenced solution removed thoroughly and carefully. Spores were suspended in 1.5 ml of physiological saline solution and repeatedly centrifuged. Spore sediment was suspended in 1 ml of saline solution and diluted 10 times and 100 times successively. 0.1 ml of the above suspension were plated on a petridish with ME agar and cultured at 28° C. for 7 days.

TABLE 1 mutants test by NTG

| Mutagen | Concentration | Treatment Minutes | Survival % |
|---------|---------------|-------------------|------------|
| NTG | 0.5 mg/ml | 10 | 4.5 |
| | | 20 | 3.0 |
| | | 30 | 2.1 |
| | | 40 | 0.8 |
| | | 50 | 0.6 |
| | | 60 | — |

The values in the given table represent percentage of survival rate of spores at the treated time after NTG exposure based on colony formation.

Influencing by UV Radiation 0.1 ml of spore suspension with spore number of the order $10^5$ and $10^4$/ml was inoculated in petridishes containing ME agar. The dishes were dried at the temperature of 28° C. for 30 minutes and then subjected to UV radiation for 20, 30, 40, 60 and 120 seconds. A fluorescent lamp, namely 30 W Philips one, was used as a source of UV radiation. It was located at a distance of 20 cm from the broth surface. The influenced dishes were then placed immediately in a dark place for 1 hour to prevent photo reactivation. The dishes were cultured at a temperature of 28° C. for 7 days.

The monocolonies having a diameter of approximately 1 cm were rinsed with 1 ml of saline solution and tested directly for rapamycin production. The primary criteria for selection of mutants for the production test were the sporulation quality and mycelium growth rate. The colonies selected were used for the screening production test Example 2

Screening Production Test

The monoisolates selected were tested for a production capability on broth having the following composition

| Dextrose | 2% |
|----------|-----|
| Ammonium sulphate | 0.1% |
| Potassium dihydrogen phosphate | 0.5% |
| Soya bean meal | 3% |
| Distilled water | pH 6.8 |

The screening production broth was inoculated with 0.5 ml of colony suspension. The sample was cultured at a temperature of 28° C. and at 220 rpm for 300 hrs and the production was then determined by means of HPLC method.

Strain: *Streptomyces hygroscopicus*
CBS 773.72, titer value: 45 mg/lt
Highest titer value colony *Streptomyces hygroscopicus* MTCC 5681, titer value: 210 mg/lt Example 3

Production Test in a Laboratory Scale at Shake Flask Level 50 ml of the inoculation broth was inoculated with 1 ml of cell suspension and cultured at the temperature of 28° C. and at 220 rpm for 96 hrs.

Composition of the Inoculation broth:

| Dextrose | 2% |
|----------|-----|
| Ammonium sulphate | 0.3% |
| Calcium carbonate | 0.15% |
| Soya bean meal | 4% |
| Distilled water | pH 6.8 |

10% of Inoculum was inoculated on the production broth. Fermentation was carried out at 28° C. and at the 220 rpm for 300 hrs. Rapamycin production was determined by HPLC method.

TABLE 2

Influence of soluble starch in the production broth of rapamycin production

| Soluble starch concentration g/L | Final PMV | Rapamycin titer mg/L MTCC 5681 | Rapamycin titer mg/L CBS 773.72 |
|---|---|---|---|
| 10 | 35 | 215 | 37 |
| 20 | 38 | 235 | 39 |
| 30 | 43 | 240 | 42 |
| 40 | 50 | 260 | 46 |
| 50 | 55 | 300 | 52 |
| 60 | 55 | 285 | 48 |

TABLE 3

Influence of dry yeast granules in the production broth to rapamycin production

| Dry yeast granules g/l | Final PMV | Rapamycin titer mg/L MTCC 5681 | Rapamycin titer mg/L CBS 773.72 |
|---|---|---|---|
| 0.5 | 55 | 300 | 49 |
| 1.0 | 55 | 310 | 53 |
| 1.5 | 60 | 350 | 55 |
| 2.0 | 52 | 280 | 51 |
| 2.5 | 45 | 250 | 48 |
| 3.0 | 40 | 222 | 45 |

TABLE 4

Influence of pH in the production broth to rapamycin production

| pH value | Rapamycin titer mg/L MTCC 5681 | Rapamycin titer mg/L CBS 773.72 |
|---|---|---|
| 4.0 | 0.00 | 0.00 |
| 5.0 | 210 | 45 |
| 5.5 | 318 | 48 |
| 6.0 | 345 | 54 |
| 6.5 | 320 | 51 |
| 7.0 | 180 | 39 |
| 7.5 | 76 | 10 |
| 8.0 | 35 | 0.00 |
| 9.0 | 31 | 0.00 |

Influence of temperature growth phase and production phase to rapamycin production

| Incubation age (hrs) | Temperature (° C.) | PMV | Rapamycin titer mg/L MTCC 5681 | Rapamycin titer mg/L CBS 773.72 |
|---|---|---|---|---|
| 0-96 | 28 | 60 | 360 | 58 |
| 96-300 | 25 | | | |
| 0-300 | 28 | 45 | 210 | 45 |
| 0-300 | 25 | 35 | 185 | 41 |

Note: Soluble starch of the optimum concentration 50 g/l in combination with the glucose was used as a carbon source. The results presented in table 3 shows that the selection of nitrogen source as the complex nitrogen dry yeast granules and is important rather than synthetic nitrogen compounds like ammonium sulphate. The results from the table 4 indicate that pH 6.0 is the optimal pH for rapamycin production. Test results also proved that temperature maintained at 28° C. in the growth phase upto 96 hrs and later on decrease of temperature to 25° C. at production phase till the end of fermentation cycle has remarkable positive influence on production capability.

Addition of shikimic acid to production media tested on 10l ts fermenter (Sartorius). Shikimic acid was used as a precursor of the substituted cyclohexane ring

| Shikimic acid concentration g/L | Rapamycin titer mg/L MTCC 5681 | Rapamycin titer mg/L CBS 773.72 |
|---|---|---|
| 0 | 350 | 55 |
| 4 | 370 | 57 |
| 8 | 410 | 61 |
| 10 | 500 | 65 |
| 12 | 340 | 55 |
| 14 | 300 | 55 |

The mutant strain of *Streptomyces hygroscopicus* MTCC 5681 produced rapamycin which was approximately by 400% higher in comparison with results achieved with the strain of *Streptomyces hygroscopicus* CBS 773.72 in all types of broths tested The content of the production broth was then optimized on the basis of the experiments presented as follows.

| | |
|---|---|
| Dextrose | 2% |
| Ammonium sulphate | 0.1% |
| Potassium dihydrogen phosphate | 0.5% |
| Soya bean meal | 3% |
| Soluble starch | 5% |
| Dry yeast granules | 0.15% |
| Shikimic acid | 1% |
| Distilled water | pH 6.8 |

This high-yielding mutant strain *Streptomyces hygroscopicus* MTCC 5681 is found suitable for commercial scale production of rapamycin.

Example 4

Mutant strain *Streptomyces hygroscopicus* MTCC 5681 was grown and maintained on ME agar comprising 1% malt extract, 0.4% yeast extract, dextrose 0.4% agar 2%, pH 7.0. Good growth was obtained after 12 days of incubation at 28° C. The spores are collected by scraping, taken into 5 ml of a normal saline solution. This suspension was used to inoculate the first stage inoculum.

First Stage Inoculum

One milliliter of above spore suspension inoculated to 500 ml Erlenmeyer flask to which 50 ml of the seed culture 1 medium described below and shake cultured on a rotary shaker (240 rpm, 1 inch stroke) at 28° C. for 4 days to prepare a seed culture 1.

Seed Culture 1 Medium (w/w %)

| | |
|---|---|
| Dextrose | 2% |
| Ammonium sulphate | 0.3% |
| Calcium carbonate | 0.15% |
| Soya bean meal | 4% |
| Distilled water | pH 6.8 |

The flasks are sterilized at 121° C. for 30 minutes and cooled to 25° C.

Second Stage Inoculum 2 liters Erlenmeyer flasks containing 400 ml seed culture 2 medium described below at pH 7.0-7.2 were sterilized by autoclaving at 121° C. for 30 minutes, cooled to 25° C. and inoculated with 14 ml of first stage inoculum, placed on a orbital shaker (2 inches stroke) set at 240 rpm and incubated for 48 hrs at 28° C.

Seed Culture 2 Medium (w/w)

| | |
|---|---|
| Dextrose | 2% |
| Soluble starch | 1% |
| Ammonium sulphate | 0.1% |
| Dipotassium hydrogen phosphate | 0.1% |
| Magnesium sulphate heptahydrate | 0.05% |
| Calcium carbonate | 0.15% |
| Soya bean meal | 4% |
| Distilled water | pH 6.8 |

Production Stage

The production stage was run in 15 L Sartorius fermenter model Biostat CDU equipped with automatic antifoam addition system and pH recorder; controller and cascade operation. The fermenter is charged with 9 L of production media consisting of the following constituents.

Production Media (w/w)

| | |
|---|---|
| Dextrose | 2% |
| Ammonium sulphate | 0.1% |
| Potassium dihydrogen phosphate | 0.5% |
| Soya bean meal | 3% |
| Soluble starch | 5% |
| Dry yeast granules | 0.15% |
| Shikimic acid | 1% |
| Distilled water | pH 6.8 |

The fermenter was sterilized at 121° C. for 30 minutes, cooled and the pH adjusted to 6.4-6.6 with sodium hydroxide. It was then inoculated with 5% of second stage inoculum and fermentation was allowed to proceed at 28° C. for 96 hrs and remaining incubation hours until harvest maintained at 25° C. with aeration and agitation in cascade mode at 40% dissolved oxygen set point.

The pH of the fermentation broth starts to drop at 96 hrs and was controlled at 6.0 until the end of fermentation by the automatic, on demand, addition of 60% glycerol solution. A titer of about 700 μg/ml determined by HPLC Waters model no WAT270008 is reached in 300 hrs. The fermentation is stopped at this point after ensuring there is no further increment in titer values.

Example 5

Mutant strain *Streptomyces hygroscopicus* MTCC 5681 was grown and spores were obtained in the same manner as described in Example 4.

First stage inoculum and second stage inoculums were obtained in the same manner as described in Example 4.

Third Stage Inoculum

There after the above-described seed culture 2 of 2.5% was inoculated to 15 L fermenter Sartorius fermenter model Biostat C-DCU 10-3 equipped with automatic antifoam addition system and pH recorder controller and cascade operation to which 10 L of seed media having the following composition has been added and sterilized.

Seed Medium (w/w)

| | |
|---|---|
| Dextrose | 2% |
| Soluble starch | 1% |
| Ammonium sulphate | 0.1% |
| Dipotassium hydrogen phosphate | 0.1% |
| Magnesium sulphate heptahydrate | 0.05% |
| Calcium carbonate | 0.15% |
| Soya bean meal | 5% |
| Yeast extract | 0.1% |
| Distilled water | pH 6.8 |

When culture was carried out at aeration 10 l pm and stirring 500 rpm at 28° C. for 48 hrs with dissolved oxygen set point 30% in cascade mode, the culture broth exhibited desired matured seed characteristics.

Production Stage

The production stage was run in 100 L Solaris fermenter model no SBS 100 equipped with automatic antifoam addition system, pH recorder controller and cascade operation. The fermenters are charged with 60 L of an aqueous production medium consisting following constituents Production Media (w/w)

| | |
|---|---|
| Dextrose | 2% |
| Ammonium sulphate | 0.1% |
| Potassium dihydrogen phosphate | 0.5% |
| Soya bean meal | 3% |
| Soluble starch | 5% |
| Dry yeast granules | 0.15% |
| Shikimic acid | 1% |
| Distilled water | pH 6.8 |

The fermenters were sterilized at 121° C. for 30 minutes, cooled and the pH adjusted to 6.4-6.6 with sodium hydroxide. It was then inoculated with 7.5% of third stage inoculum and fermentation was allowed to proceed at 28° C. for 96 hrs and remaining incubation hours until harvest maintained at 25° C. with aeration and agitation in cascade mode at 40% dissolved oxygen set point.

The pH of the fermentation broth starts to drop at 96 hrs and was controlled at 6.0 until the end of fermentation by the automatic, on demand, addition of 60% glycerol solution. A titer of about 900 μg/ml, determined by HPLC was attained in 300 hrs. The fermentation was stopped at this point after ensuring there was no further increment in titer values.

We claim:

1. A mutant strain *Streptomyces hygroscopicus* MTCC 5681 derived from wildtype *Streptomyces hygroscopicus*.

2. The mutant strain according to claim 1 wherein said strain is capable of producing rapamycin at a titer value of about 900 mg/L during cultivation.

3. A process for the submerged fed batch production of rapamycin which comprises cultivating a microorganism as defined in claim 1.

4. A process as claimed in claim 3, wherein the feeding for fed batch fermentation is done to maintain pH at 6.0 for about 96 hours or when the pH tends to rise.

5. A process as claimed in claim 3, wherein the feed solution is 60% glycerol or 10% soluble starch.

6. A process as claimed in claim 3, wherein precursor shikimic acid is added as a feed solution.

7. A process for the manufacture of rapamycin comprising steps of:
   i. preparing an inoculum of a mutant strain Streptomyces hygroscopicus MTCC 5681 of claim 1;
   ii. developing the seed stages with the said inoculum; and
   iii. inoculating the said matured seed to fermenter to obtain rapamycin.

8. A process for producing rapamycin which comprises culturing in a nutrient medium a mutant strain capable of producing rapamycin, wherein said mutant strain is *Streptomyces hygroscopicus* MTCC 5681 of claim 1 under submerged fermentation conditions.

9. A process as claimed in claim 8, wherein the nutrient medium comprises a carbon source, a nitrogen source and a precursor.

10. A process claimed in claim 9, wherein said carbon source is in the form of a combination of glucose and soluble starch, the combination featuring 2% of glucose and 5% of soluble starch.

11. A process claimed in claim 9, wherein said nitrogen source contains soya flour and dry yeast granules as a complex nitrogen source.

12. A process claimed in claim 9, wherein the nutrient medium comprises precursor shikimic acid.

13. A process claimed in claim 7, wherein the temperature of the fermentation process is set at 28° C. up to 96 hours and set at 25° C. for the rest of fermentation cycle.

* * * * *